United States Patent [19]

Burnett

[11] Patent Number: 5,719,503
[45] Date of Patent: Feb. 17, 1998

[54] DETECTION OF SURFACE ANOMALIES IN ELONGATE CONDUCTIVE MEMBERS BY PULSE PROPAGATION ANALYSIS

[75] Inventor: Gale D. Burnett, Lynden, Wash.

[73] Assignee: Profile Technologies, Inc., Lynden, Wash.

[21] Appl. No.: 747,195

[22] Filed: Nov. 12, 1996

Related U.S. Application Data

[63] Continuation of Ser. No. 403,334, Mar. 14, 1995, abandoned.

[51] Int. Cl.$^6$ .................................................. G01R 31/08
[52] U.S. Cl. ........................... 324/534; 324/637; 324/642; 324/532
[58] Field of Search ................................... 324/637, 642, 324/532, 534, 644, 535, 533, 639; 379/2, 5, 26

[56] References Cited

U.S. PATENT DOCUMENTS

| | | |
|---|---|---|
| 1,745,419 | 2/1930 | Henneberger . |
| 2,113,749 | 4/1938 | Statham . |
| 2,522,362 | 9/1950 | Gilbert . |
| 2,570,912 | 10/1951 | Bishop . |
| 2,602,834 | 7/1952 | Leslie et al. . |
| 2,725,526 | 11/1955 | Stringfield et al. . |
| 2,731,598 | 1/1956 | Herbert . |
| 2,887,652 | 5/1959 | Bendayan et al. . |
| 3,526,831 | 9/1970 | Smith . |
| 3,600,674 | 8/1971 | Roberts . |
| 3,609,533 | 9/1971 | Pardis . |
| 3,909,712 | 9/1975 | Rietz et al. . |
| 3,924,179 | 12/1975 | Dozier . |
| 4,039,938 | 8/1977 | Link . |
| 4,063,161 | 12/1977 | Pardis . |
| 4,099,117 | 7/1978 | Erath . |
| 4,112,349 | 9/1978 | Weber . |
| 4,118,662 | 10/1978 | Weber . |
| 4,255,710 | 3/1981 | Weber . |
| 4,289,019 | 9/1981 | Claytor . |
| 4,291,204 | 9/1981 | Crick . |
| 4,404,514 | 9/1983 | Reichert, Jr. . |
| 4,538,103 | 8/1985 | Cappon . |
| 4,739,276 | 4/1988 | Graube . |
| 4,755,742 | 7/1988 | Agoston et al. . |
| 4,829,284 | 5/1989 | Pfaff . |
| 4,855,656 | 8/1989 | Saitoh et al. . |
| 4,929,896 | 5/1990 | Lara . |
| 4,970,467 | 11/1990 | Burnett . |
| 5,070,537 | 12/1991 | Ohira et al. . |
| 5,087,873 | 2/1992 | Murphy et al. . |
| 5,126,654 | 6/1992 | Murphy et al. . |
| 5,189,374 | 2/1993 | Burnett . |
| 5,243,294 | 9/1993 | Burnett . |
| 5,270,661 | 12/1993 | Burnett . |

FOREIGN PATENT DOCUMENTS

3533479   3/1987   Germany .

*Primary Examiner*—Vinh P. Nguyen
*Assistant Examiner*—Jose M. Solis
*Attorney, Agent, or Firm*—Michael R. Schacht; Hughes, Multer & Schacht, P.S.

[57] ABSTRACT

Pulse propagation analysis to ascertain whether an anomaly such as surface corrosion exists on a section of conductive member such as pipe. Anomalies such as surface corrosion result in localized velocity changes of pulses, due to inherent nonlinearities, propagating along a conductive member. These localized velocity changes exhibit themselves in changes in waveform, rise and fall time, amplitude, and time delay of a pulse with respect to a fixed time reference. To allow such anomalies to be located, two pulses are generated such that they intersect at intersecting locations along the conductive member. The resulting modified pulses are analyzed for perturbations indicative of localized velocity changes.

30 Claims, 8 Drawing Sheets

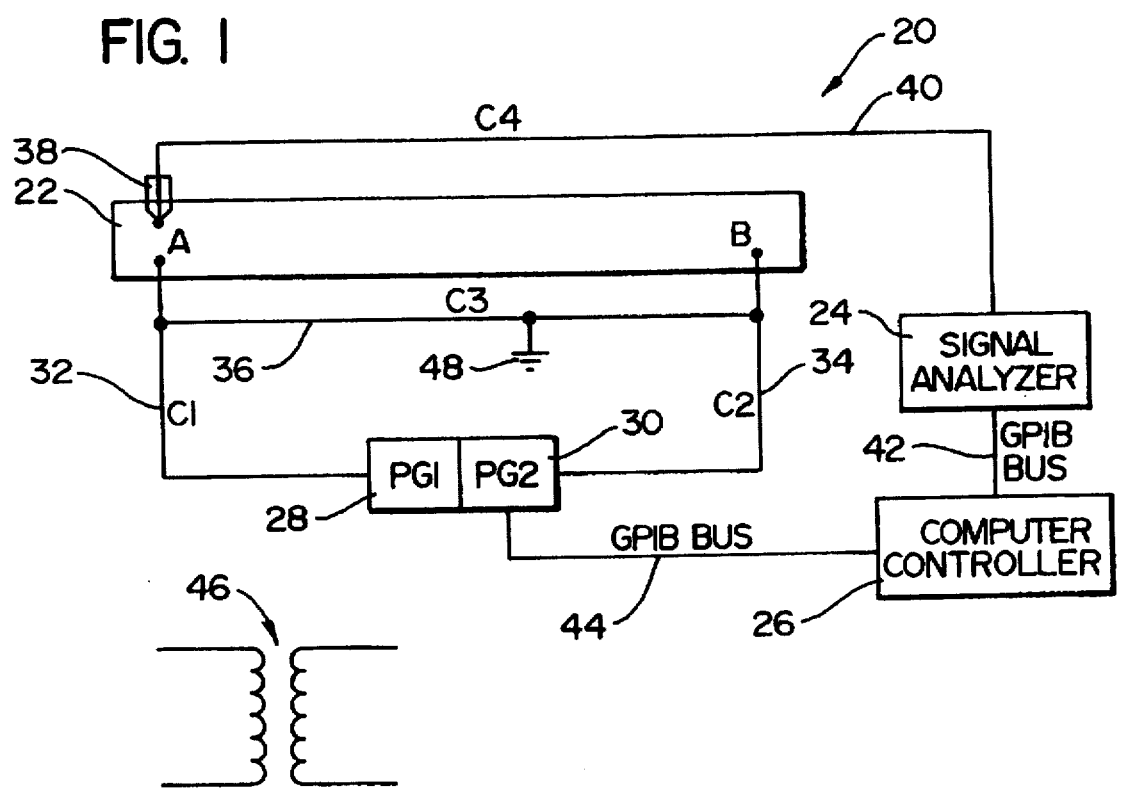

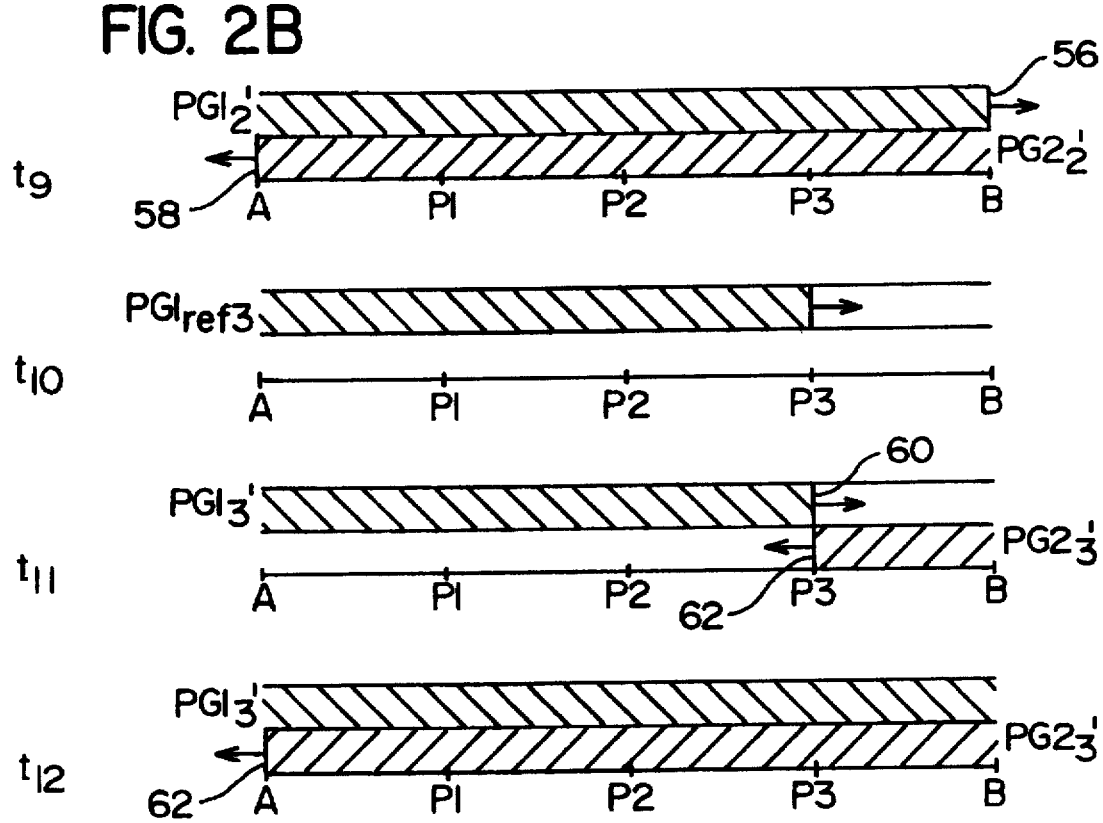

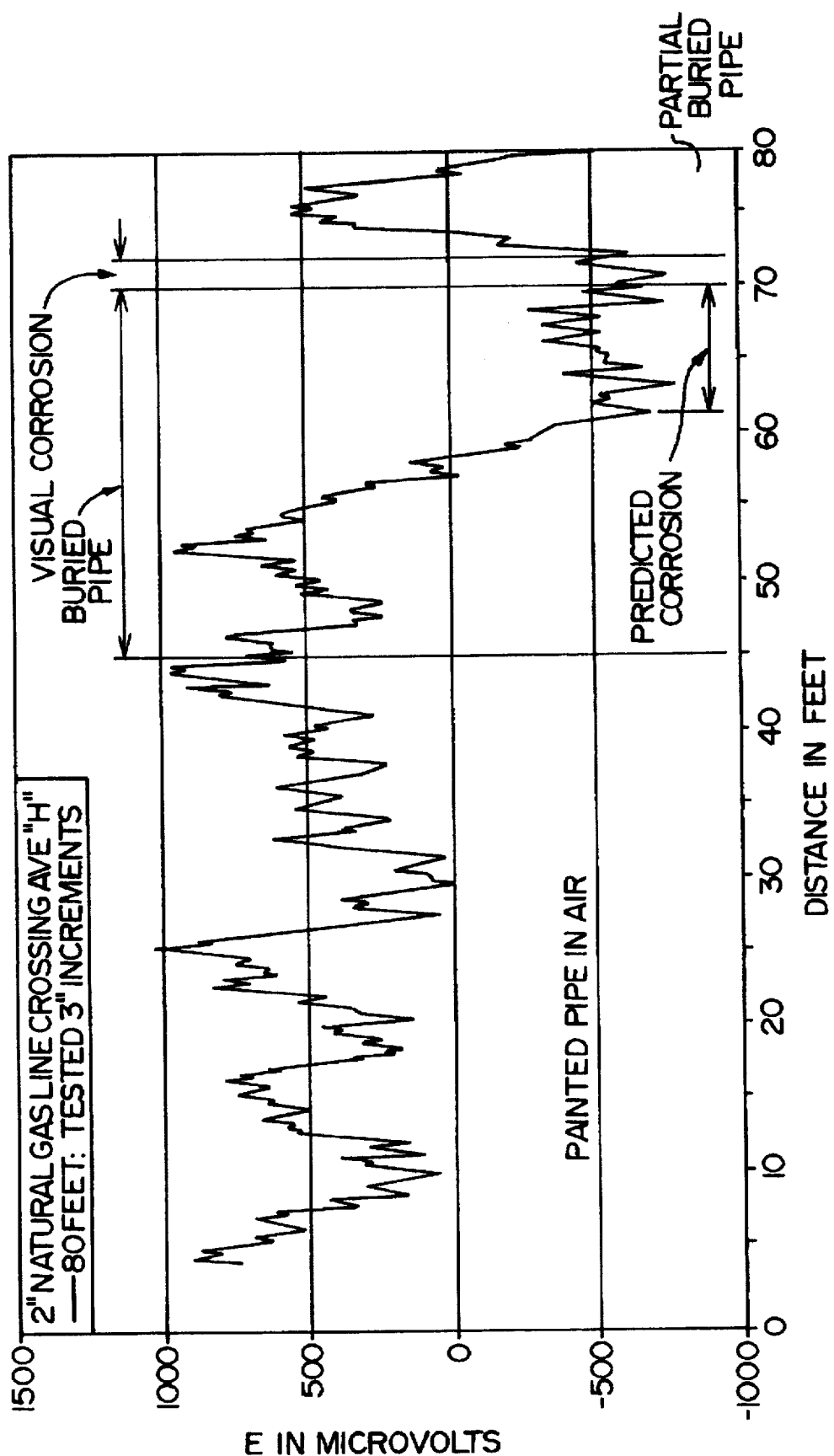

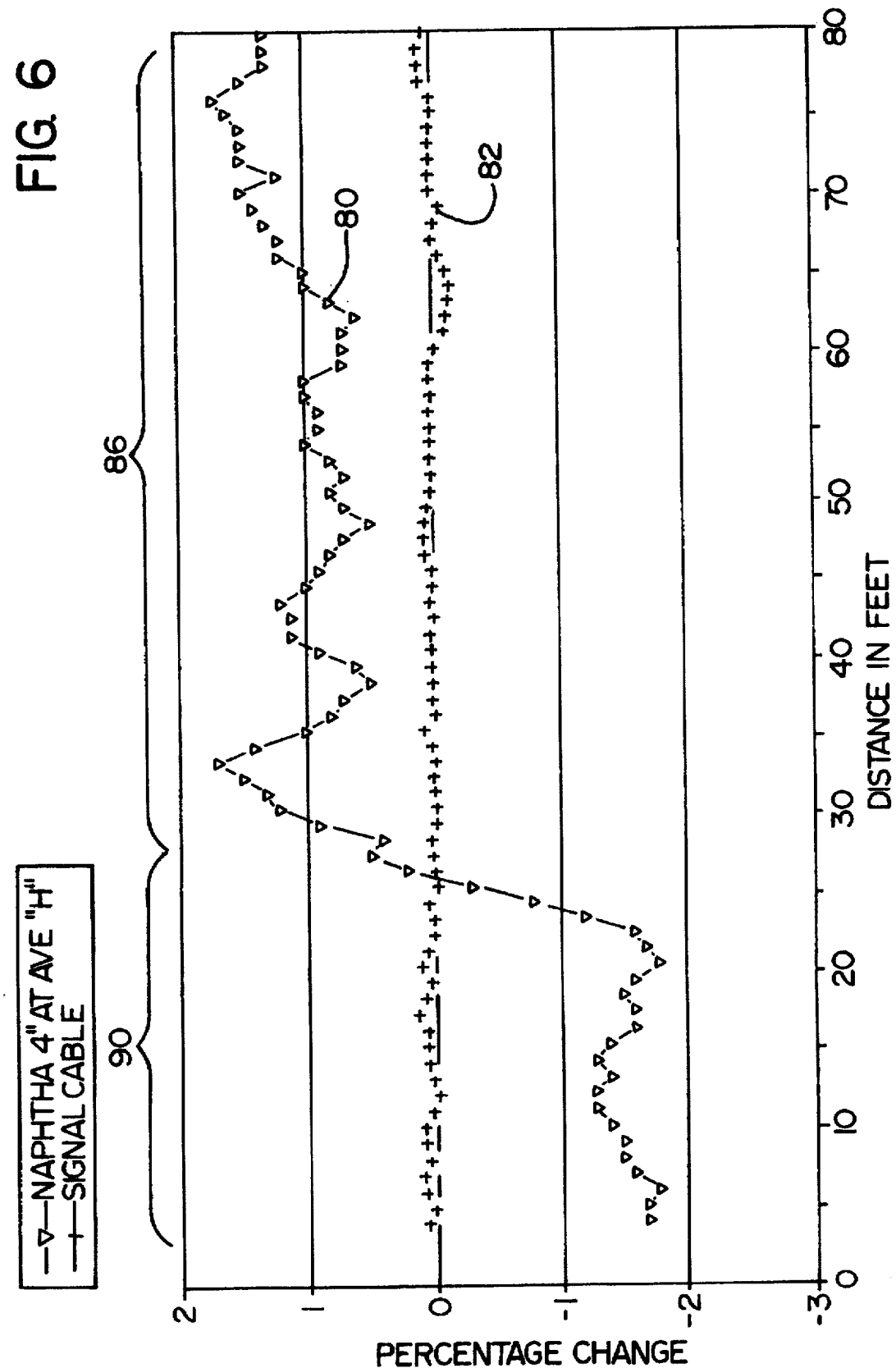

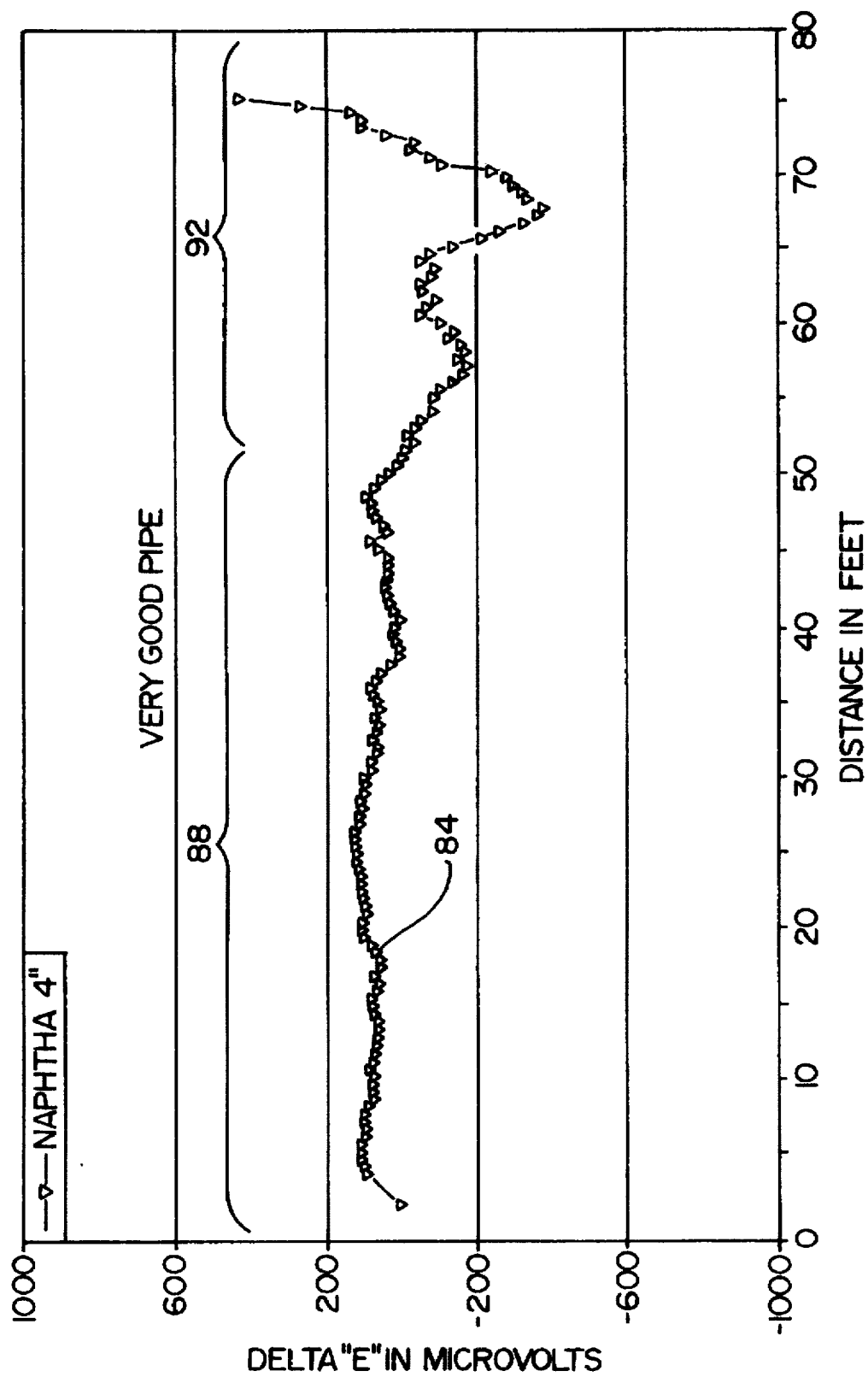

DETECTION OF SURFACE ANOMALIES IN ELONGATE CONDUCTIVE MEMBERS BY PULSE PROPAGATION ANALYSIS

This is a continuation of application Ser. No. 08/403,334 filed on Mar. 14, 1995, now abandoned.

TECHNICAL FIELD

The present invention relates to pulse propagation analysis and, more particularly, to the analysis of one of two intersecting electrical pulses to determine whether a surface anomaly exists at the location where the two pulses intersect.

BACKGROUND OF THE INVENTION

Pulse propagation analysis has long been proposed as a tool for nonintrusively detecting anomalies in elongate, conductive members such as buried cables and the like. In U.S. Pat. No. 4,970,467, the present applicant proposed propagating two electrical pulses along a conductor such that they intersect at a predetermined location along the conductor. By analyzing one of these pulses after they have passed through the predetermined location, the applicant found that the presence or absence of an anomaly at the predetermined location could be predicted.

The basic principle disclosed in the '467 patent was also used in U.S. Pat. Nos. 5,189,374, 5,243,294, and 5,270,661, all also issued to the present applicant. The '374 patent applied the basic principles described in the '467 patent in the context of a conductive member, such as a well casing, where one end of the member is more accessible than the other end. The '294 patent teaches that the propagation delay for the length of the conductive member under test can be used to set the timing of the pulses such that the pulses intersect at a plurality of desired locations along the portion of the conductive member under test. The '661 patent teaches applying a DC electrical current to the member to provide an electrical potential. Changes in the electrical potential are observed and correlated with analysis of pulses that have intersected along the member.

While the basic principles described in the foregoing patents are generally applicable to any conductive member, the inventions claimed in those patents were, for illustration purposes, disclosed in the context of a buried pipe. In contrast, the present invention is of particular significance when used in the context of detecting surface anomalies, such as corrosion, on insulated pipe located above ground. Accordingly, that application will be described in detail herein. The present invention may, however, have broader application to detecting other anomalies on elongate, conductive members. The scope of the present invention should thus be determined not based on the following detailed description but instead on the claims appended hereto.

In manufacturing facilities such as oil refineries and the like, miles of pipe are used to carry fluids being processed or used in the refining process. The failure of such pipes can cause extensive damage, and these pipes are often routinely inspected to avoid pipe failures and the damage resulting therefrom. For a variety of reasons, such as energy conservation and worker safety, many of these pipes are wrapped with insulation.

For any given pipe, the entire interior surface of the pipe is subject to essentially the same conditions. The interior of the pipe thus can be satisfactorily tested by sampling analysis of the interior surface at discrete points and using statistical analysis to draw inferences regarding the condition of the pipe at locations between the sampled points.

The exterior surface of insulated pipe cannot be adequately tested using sampling and statistical inferences, however, because one cannot assume that the entire exterior surface of insulated pipe is subject to the same conditions. To the contrary, anomalies on the exterior surface of a pipe tend to be localized and caused by factors specific to that location.

Accordingly, to inspect the exterior surface of insulated pipes, the insulation must be removed and the exterior surface visually inspected. The process of removing and reinstalling this insulation is very expensive. In this context a buried pipe will be considered one form of insulated pipe, as buried pipe cannot be visually inspected without expensive excavation. Accordingly, the need exists for a method of testing the condition of the exterior surface of an insulated pipe by means other than visual inspection after the insulation has been removed.

OBJECTS OF THE INVENTION

From the foregoing, it should be apparent that one specific object of the present invention is to provide methods and apparatus than allow a surface anomalies in a length of pipe to be detected and located.

Another more specific object of the present invention is to provide pulse propagation systems and methods having a favorable mix of the following characteristics:

(a) allows unobtrusive testing of elongate conductive members such as pipes and the like;

(b) obviates the need to visually inspect pipe such as insulated pipe that is not easily visually inspected; and (c) can be effectively and consistently applied in a cost efficient manner.

SUMMARY OF THE INVENTION

By empirically testing under controlled conditions sections of pipe that are identical accept for the fact that one pipe has surface corrosion and the other pipe does not, the applicant has determined that corrosion on the surface of a pipe yields a measurable change in propagation velocity, rise time, and amplitude of an electrical pulse passing through a section of pipe having surface corrosion. While these parameters will vary somewhat even in good pipe, the variations are noticeably more severe when the pipe has surface corrosion thereon.

The applicant thus concluded that the effect of corrosion on propagation of velocity, rise time, and amplitude of single pulse should also be observable in some form in a pulse that has intersected another pulse at a predetermined location. By looking for the affects of corrosion in a two-pulse system, not only can corrosion be identified but it can also be located and significantly simplifies the testing process.

The present invention in its most basic form is thus a method of detecting an anomaly of conductive member comprising the steps of sending an electrical pulse along the conductive member and analyzing characteristics of the pulse such as propagation speed, rise time, waveform shape, and amplitude to ascertain whether corrosion exists on the conductive member. By comparing these characteristics to those generated for a known good pipe, the absence or presence of an anomaly can be predicted.

In another exemplary form, the present invention is a method of detecting corrosion on the surface of a pipe. In this situation, it is not only desirable to detect the presence or absence of an anomaly, but to ascertain the location of the anomaly along the length of pipe.

To allow an anomaly not only to be detected but to be located, the present invention comprises the steps of sending two electrical pulses along the conductive member such that they intersect at an intersecting location and analyzing at least one characteristic of at least one of the pulses after they have passed through the intersecting location to determine whether an anomaly exists at the intersecting location. To provide information related to corrosion, the pulse characteristic that is analyzed should provide an indication of localized velocity changes of the pulse along the given section of pipe. To this end, such factors as the propagation delay, rise time of the leading edge, and amplitude of the pulse may be considered to determine whether corrosion exists.

To provide a complete picture of an entire length of pipe, a plurality of pulses are timed to intersect at different predetermined locations along the length of pipe. Then, one pulse associated with each predetermined location is analyzed to determine whether an anomaly exists at the predetermined location.

While a combination of characteristics of a given pulse may be analyzed to determine corrosion, the applicant has found that the most observable, with currently available test equipment limitations, indications of surface anomalies are contained at or near the leading edge of the pulse. The rise time of the leading edge, the amplitude of the pulse adjacent to the leading edge, the shape of the leading edge as compared to the shape of the leading edge for pulses generated at known good locations, and whether the leading edge is shifted from a predicted position in time all may indicate the presence or absence of surface anomalies at the intersecting location.

In practice, the applicant has found that electrically connecting the points on a conductive member at either end of the section of interest removes certain variables relating to grounding and substantially reduces the amount of power required to generate a given pulse. By referring all test equipment to a reference potential set at the potential of the electrically connected end points, very low power pulses may be used. Low power pulses appear to provide more meaningful information related to the surface of the pipe than do higher power pulses.

Additionally, the applicant has found that, especially for short lengths of pipe, the widths of the pulses used should be much greater than the propagation delay between the end points of the portion of the conductive member in question. By selecting a pulse width at least ten times the length of the propagation delay, the leading edge of the pulse is isolated from the trailing edge thereof. This is because for short pipe lengths, equipment limitations in the development of short duration pulse widths can result in ringing at the leading and trailing edges which obscure the effects on the pulse waveform caused by surface anomalies.

As generally described above, the present invention results in an unobtrusive test for exterior corrosion that can be performed with high resolution along a length of covered pipe simply by providing access to the end points of the section of pipe in question. The present invention thus obviates the need to remove insulation or dig up pipe for the purpose of visually inspecting the exterior thereof. Other objects and advantages of the present invention will become apparent from the following detailed description.

BRIEF DESCRIPTION OF THE DRAWINGS

FIG. 1 of the drawing is a schematic depiction of a system for implementing the processes of the present invention;

FIGS. 2A and 2B are timing diagrams schematically depicting the generation and interaction of the pulses employed to ascertain whether anomalies exist along a given length of pipe;

FIGS. 5-7 are graphs showing how certain characteristics of modified pulses may be plotted to help determine whether the modified pulses contain data indicative of surface anomalies.

DETAILED DESCRIPTION OF THE INVENTION

Figure 2A:
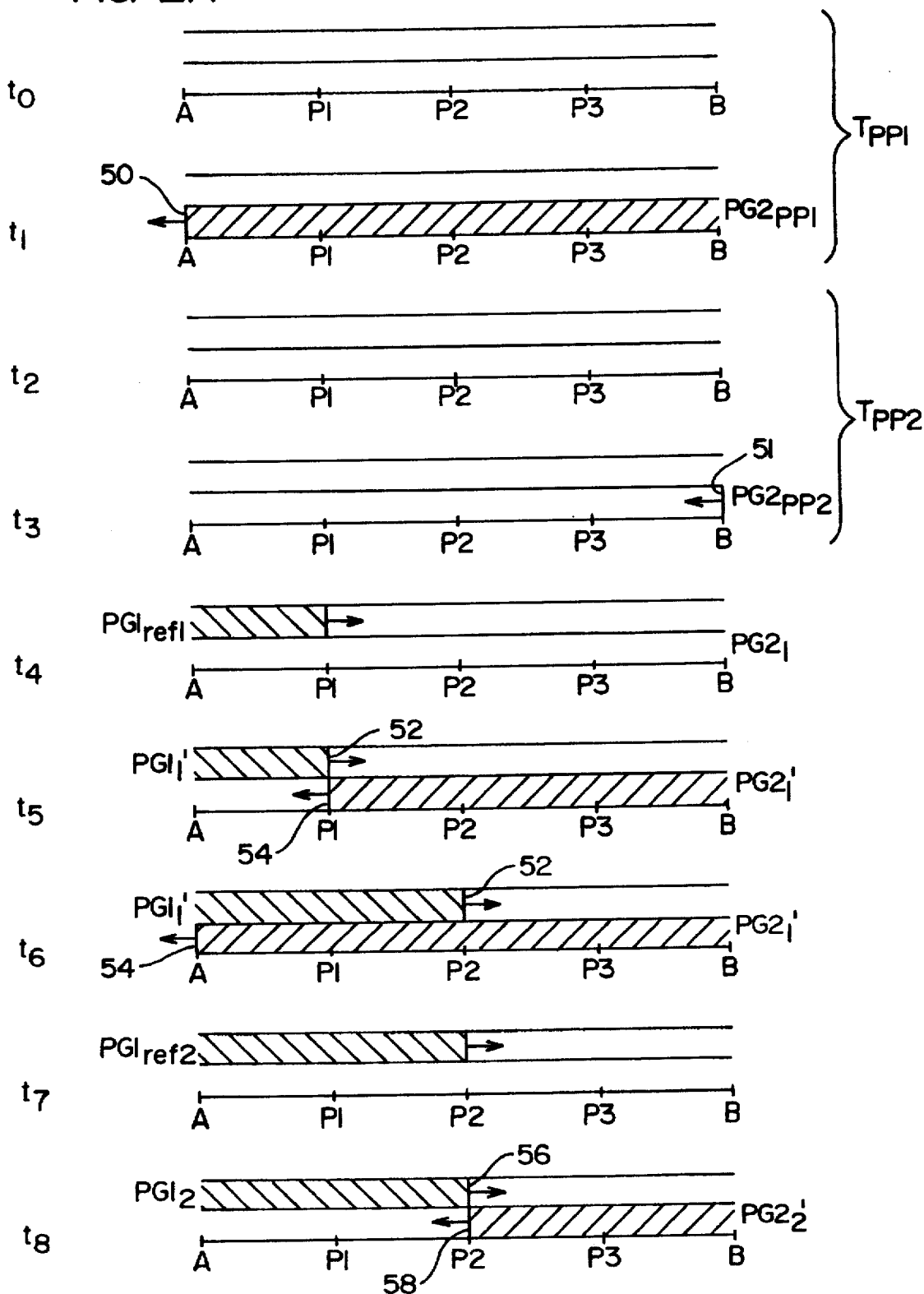

Referring now to the drawing, depicted in FIG. 1 is a system 20 constructed in accordance with, and embodying, the principles of the present invention. The system 20 is configured to measure for surface anomalies on a pipe 22 between points A and B located on that pipe.

The system 20 basically comprises a digital signal analyzer 24, and computer controller 26, a first pulse generator 28, and second pulse generator 30. The output of the first pulse generator 28 is connected to the point A by a cable 32. The second pulse generator 30 is connected to the point B by a cable 34. A cable 36 is connected between the points A and B on the pipe 22.

The signal analyzer 24 is connected to a probe 38 via a cable 40. The computer controller is connected to the signal analyzer 24 by a GPIB bus 42 and to the pulse generators 28 and 30 by a GPIB bus 44. The generation of pulses by the pulse generators 28 and 30 and detection of these pulses by the signal analyzer 24 are controlled by the computer controller 26. The logic implemented by the computer controller will be discussed below, and the steps required to implement this logic will be clear to one of ordinary skill in the art of computer controlled test equipment.

Also employed in the system 20 is an isolation transformer 46 that isolates the system 20 so that the signal analyzer 24, computer controller 26, and pulse generators 28 and 30 may be referenced to a floating reference point identified at 48 and connected to the cable 38.

This arrangement of floating the test signals isolates these signals from the noise introduced by the various grounded pipes in a refinery setting. While this arrangement renders the system 20 less suitable for measuring the interaction between the pipe 22 and its environment, it greatly enhances the ability of system 20 to test the condition of the pipe itself in a refinery setting.

Referring now to FIGS. 2A and 2B, depicted in these Figures are highly schematic graphs depicting the propagation and interaction of pulses generated by the pulse generators 28 and 30. FIGS. 2A and 2B contain a total of thirteen separate graphs, each of which is associated with a given time. For reference purposes, each of these graphs is identified by the time $t_0$ through $t_{12}$ associated therewith. These points in time $t_0$ through $t_{12}$ increase in time in sequential order.

In the following discussion, these graphs will be discussed in sequence to provide one simple example illustrating the basic operation of the present invention. In these graphs, end points A and B of the section of the pipe 22 in question are shown, along with three points P1 P2, and P3 on the pipe 22 between the end points A and B. The point P2 is midway between the points A and B. The point P1 is midway between the points A and P2, while the point P3 is midway between the points P2 and B. It should be clear that any number and spacing of points may be used as required by a given length and configuration of pipe.

Pulses generated by the first pulse generator 28 are shown in an upper half of these graphs and identified by the term PG1, while pulses generated by the second pulse generator 30 are shown in the lower half of the graph and identified by the term PG2. Subscripts are used to distinguish the various pulses generated by the pulse generators 28 and 30 and will be identified in the text.

A vertical line with a horizontal arrow adjacent thereto indicates the leading edge of any given pulse. The direction of the arrow indicates the direction of propagation of the pulse. Lines slanted to the left indicate the presence of a pulse generated by the first pulse generator 28 at a given point and at a given time, while rightwardly slanted lines indicate the presence of a pulse generated by the second pulse generator 30 at a given location on the pipe at a given point in time.

Additionally, during and after a given pulse intersects another pulse, the given pulse will be identified by a prime (') mark and will be referred to as a modified pulse. Any pulse that traverses the pipe 22 between points A and B may be referred to as an unmodified pulse as long as it does not intersect another pulse.

While in theory the present invention can be applied on a pulse-by-pulse basis, practically a number of pulses are sampled and averaged to store a given waveform. This sampling and averaging process will be described in further detail in the following discussion.

Referring now to the drawings, the first basic step in the process of the present invention is illustrated by graphs associated with times $t_0$ through $t_3$. This first step has two basic purposes: first, a waveform of an unmodified pulse generated by the second pulse generator, applied to point B, and measured at point A, is stored to provide a reference waveform and time reference for subsequent analysis; and, certain time intervals are measured to determine the propagation delay for a pulse traversing the pipe 20 between points A and B.

More particularly, $t_0$ indicates the point in time at which a pulse $PG2_{pp1}$ is generated by the second pulse generator 30. Because of propagation delays in cables and the like, this pulse $PG2pp_1$ is not yet present on the pipe 22.

At time $t_1$, the pulse $PG2_{pp1}$ has traversed the pipe and its leading edge 48 has reached the point A. At this time $t_1$, the waveform of the pulse $PG2_{pp1}$ is sampled. As mentioned above, this sampling process is actually performed by generating a plurality of pulses PG2 and averaging these pulses to obtain the unmodified pulse $PG2pp_1$. The time interval between the times $t_0$ and $t_1$ is also recorded and will be referred to as $T_{pp1}$. At the time $t_1$, the probe 38 is in contact with the point A on the pipe 22.

The probe 38 is next moved to the point B on the pipe 22. Then, at time $t_2$, another pulse $PG2_{pp2}$ is generated by the second pulse generator 30. This leading edge 51 of this pulse $PG2_{pp2}$ reaches the point B at a time $t_3$. Again, a plurality of PG2 pulses are generated to obtain the pulse $PG2_{pp2}$. The interval between the time $t_2$ and $t_3$ will be referred to as $T_{pp2}$.

The propagation delay $T_{ab}$ of an electrical signal moving between points A and B along the pipe 22 may be calculated from the following formula:

$$T_{ab}=T_{pp1}-T_{pp2} \quad \text{(EQUATION 1)}$$

By calculating the propagation delay $T_{ab}$ in this manner, the various propagation delays throughout the system 20 can be calculated for the purposes of determining the timing and sequencing of the pulses discussed below. Given the teachings of U.S. Pat. No. 5,243,294, which are incorporated herein by reference, the use of the propagation delay $T_{ab}$ to determine timing and sequencing set forth below should be apparent to one of ordinary skill in the art, and the exact timing and sequencing used in the example shown in FIGS. 2A and 2B will not be described herein in detail.

The next step is to generate modified pulses for each of the points P1, P2, and P3 spaced along the pipe 22. This is accomplished basically as follows.

Between the times $t_3$ and $t_4$ in FIG. 2A, the probe 38 is returned to the point A along the pipe 22. Based on the propagation delay $T_{ab}$, a pulse $PG1_{ref1}$ is stored to provide a reference pulse for later processing. As before, the stored pulse $PG1_{ref1}$ is actually calculated from a plurality of pulses that have been sampled and averaged.

Between times $t_4$ and $t_5$, pulses $PG1_1$ and $PG2_1$ are generated by the first and second pulse generators 28 and 30. Based on the propagation delay $T_{ab}$, these pulses $PG1_1$ and $PG2_1$ are timed such that leading edges 52 and 54 of the pulses $PG1_1$ and $PG2_1$ intersect at time $t_5$ at the point P1 along the pipe 22; the point P1 is a first intersecting point.

Next, at time $t_6$, the leading edge 54 of the modified pulse $PG2_1'$ reaches the point A and a waveform $WFA_1$ present at point A is sampled and stored by the signal analyzer 24. Again, this sampling and storing process requires the sampling of a series of waveforms that are averaged to obtain the waveform $WFA_1$.

Subsequently, between the points $t_6$ and $t_7$, a second reference pulse $PG1_{ref2}$ is generated. At time $t_7$, the reference pulse $PG1_{ref2}$ is stored. Again, this pulse $PG1_{ref2}$ is actually calculated from a plurality of pulses that have been sampled and averaged.

Between times $t_7$ and $t_8$, pulses $PG1_2$ and $PG2_2$ are generated by the pulse generators 28 and 30. At time $t_8$, leading edges 56 and 58 of the pulses $PG1_2$ and $PG2_2$ intersect at point P2 along the pipe 22. The point P2 corresponds to a second intersecting location. At time $t_9$, a waveform $WFA_2$ present at point A is sampled and stored by the signal analyzer 24 in the same manner as the waveform $WFA_1$ described above.

Between the points $t_9$ and $t_{10}$, a third reference pulse $PG1_{ref3}$ is generated. Again, this pulse $PG1_{ref3}$ is actually calculated from a plurality of pulses that have been sampled and averaged.

Finally, between the times $t_{10}$ and $t_{11}$, pulses $PG1_3$ and $PG2_3$ are generated by the first and second pulse generators 28 and 30. At time $t_{11}$, leading edges 60 and 62 of these pulses $PG1_3$ and $PG2_3$ intersect at point P3. The point P3 is a third intersecting location. Then, at time $t_{12}$, a waveform $WFA_3$ at point A is sampled and stored by the signal analyzer 24.

The waveforms $WFA_1$, $WFA_2$, and $WFA_3$ sampled and stored at point A at times $t_6$, $t_9$, and $t_{12}$ all contain information that can be used to predict the existence or absence of an anomaly at the points P1 P2, and P3, respectively. More particularly, these stored waveforms $WFA_1$, $WFA_2$, and $WFA_3$, all comprise a component contributed by the leading edge of one of the modified pulses $PG2_1'$, $PG2_2'$, and $PG2_3'$.

The applicant has found that, by analyzing and/or processing these waveforms $WFA_1$, $WFA_2$, and $WFA_3$, information can be extracted from these waveforms that will allow anomalies, and especially surface corrosion, to be predicted at the intersecting locations associated with the points P1, P2, and P3.

In particular, characteristics of the leading edge of the modified pulses PG2' can be extracted from the waveforms WFA. These characteristics can be analyzed for variations that can be predictors of anomalies at the intersection points where the pulses PG2 intersected the pulses PG1. Accordingly, the existence and location of problem spots such as surface corrosion along a given length of insulated pipe can be predicted. This location can then be visually inspected and repaired if necessary.

On the other hand, the applicant also believes that the absence of problems such as corrosion can be predicted with an acceptable degree of certainty along the length of a pipe, which may obviate the need visually to inspect the entire length of pipe.

The characteristics of the leading edge of the modified pulses that suggest surface anomalies along the length of the pipe include the amplitude of the modified pulse adjacent to the leading edge, the rise time and shape of the leading edge, and time displacements of this leading edge relative to a predicted location of the leading edge.

The empirical data suggests that the propagation velocity of a given electrical signal passing through a given length of pipe is dependent upon the condition or makeup of the surface of the pipe. More particularly, if the pipe surface is steel, the propagation velocity will be one value, while if the surface of the pipe is oxidized steel (corroded), the propagation velocity of the electrical pulse will be another value. The applicant believes that these differing localized propagation velocities are manifested not only by a relative displacement of the leading edge as compared against a fixed time reference, but by the shape of the leading edge as evidenced by rise time and amplitude adjacent to the leading edge.

Extracting this information from the waveforms WFA sampled and stored as described above is complicated by several factors, however.

In particular, in a refinery setting where pipe runs are relatively short, the Applicant has determined that the pulse widths of the pulses employed should be significantly longer than the propagation delay across the section of pipe of interest. Pulse lengths of approximately the same duration as the propagation delay result in interference between the leading edge of a pulse arriving at one end of the pipe section and the trailing edge of another pulse leaving that end of the pipe section. This interference can obscure information contained in the leading edge of the pulse being analyzed.

Ideally, the pulse width would be much smaller than the propagation delay across the pipe section of interest. While pulses of such short durations can be generated, these pulses generated by currently available test equipment contain a significant amount of ringing that can also obscure the information contained in the leading edge of the pulse of interest.

Accordingly, the Applicant employs pulse widths than are either: much longer than the propagation delay of the pipe section of interest to avoid the problems with pulses equal to or shorter than the propagation delay for short pipe runs; or much shorter than the propagation delay of the pipe section of interest when a reliable pulse can be generated relative to the propagation delay.

In practice, with short propagation delays, the Applicant will normally use a pulse width of at least ten times the propagation delay, and often one that is a hundred or a thousand times the propagation delay. With long propagation delays where pulse widths of less than the propagation delay are feasible, the Applicant will use a pulse width of at most one tenth of the propagation delay. The examples described herein presume short pipe lengths and short propagation delays that prevent the use of pulse widths of less than the propagation delay.

The use of pulse widths that are greater than the propagation delay means that, when a leading edge reaching a given end of a pipe section is being analyzed, the pulse generated at that given end is still present at the given end. This situation is shown, for example, at time $t_6$ in FIG. 2A. At time $t_6$ when the waveform $WFA_1$ is being sampled and stored, the pulse $PG1_1'$ and the leading edge 54 of the pulse $PG2_1'$ are both present at the location A.

To compensate for the contribution of the pulse $PG1_1'$, the waveform $WFA_1$ is modified by the waveform of the pulse $PG1_1$. In particular, the pulse $PG1_{refl}$ waveform snored an time $t_4$ is subtracted from the waveform $WFA_1$ stored at time $t_6$. This process results in a processed waveform $WFA_1'$ that primarily reflects the contribution of the leading edge 54 of the pulse $PG2_1'$ and not that of the pulse $PG1_1'$.

The processed waveform WFA' can thus be analyzed for rise time, amplitude, and time shift characteristics of one of the modified pulses PG1' or PG2' to ascertain whether anomalies such as corrosion exist at the intersecting location associated therewith.

Additionally, this waveform is compared against the waveform $PG2_{pp1}$ stored at time $t_1$. The waveform $PG2_{pp1}$ represents the shape and timing of an unmodified pulse passing through intersecting location, and the comparison of waveform shape, rise time, and time delay of the $PG2_{pp1}$ and WFA' waveforms indicates the presence or absence of an anomaly at a given intersecting location.

EXAMPLE 1

Figure 3:
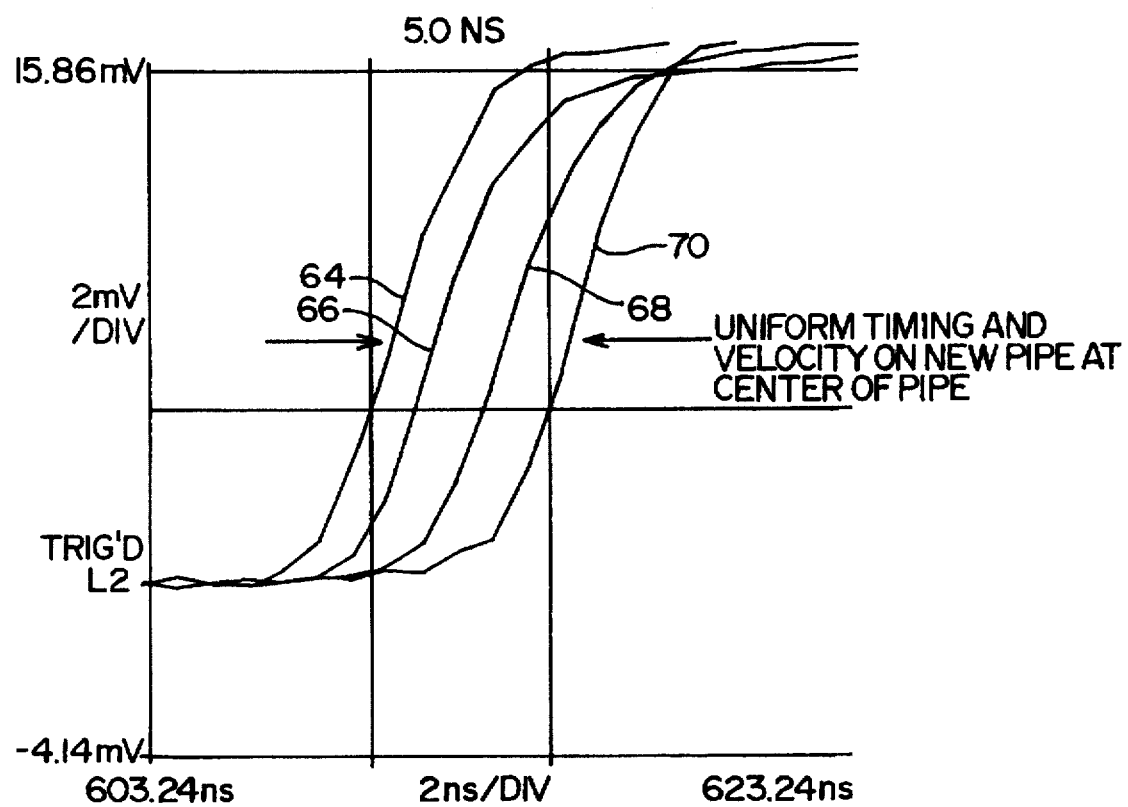
FIGS. 3 and 4 are graphs showing how surface anomalies such as corrosion affect the leading edge of electrical pulses traversing known good and know bad pipes under controlled conditions.
Figure 4:
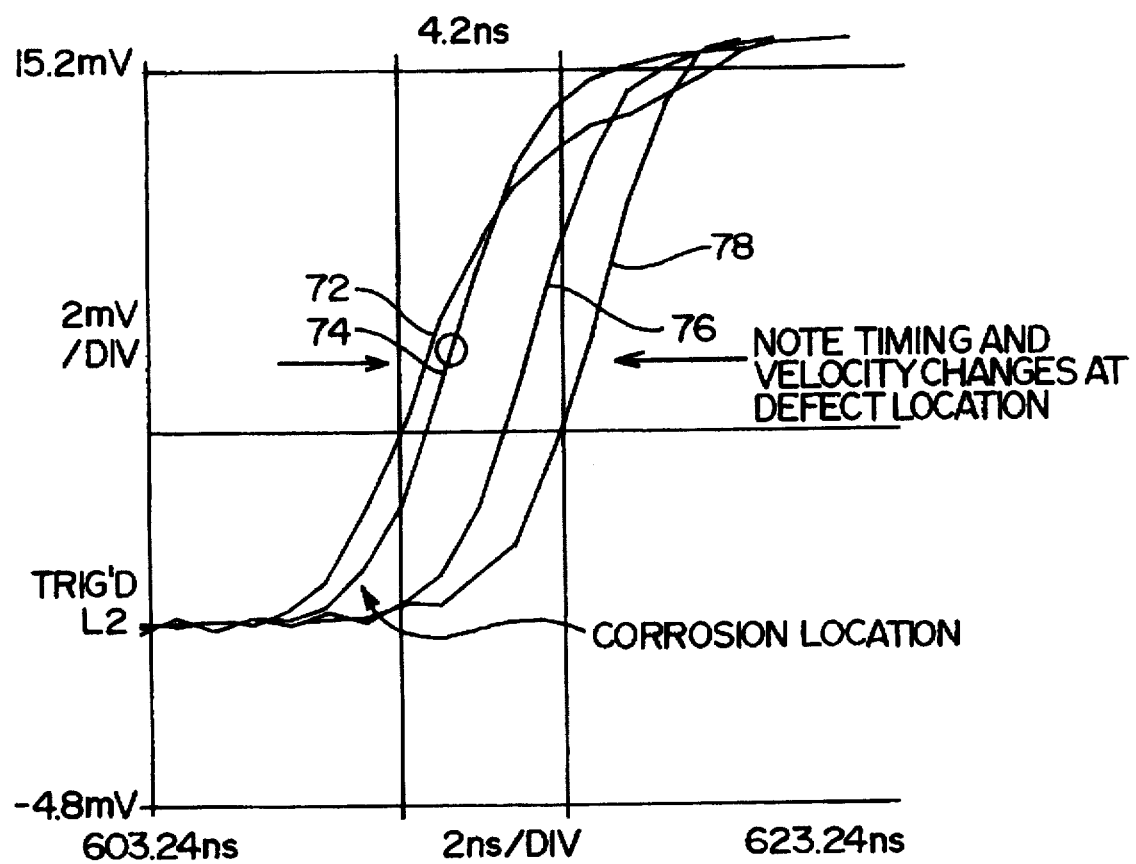

Referring now to FIGS. 3 and 4, depicted therein are signal analyzer traces showing the leading edges of a several pulses that have been passed through known good and known bad pipe under controlled conditions in a laboratory. These traces show that the pulses through the known bad pipe differ significantly from those of the known good pipe.

In this example, a single pulse was propagated through the pipe under test. The pulse was measured at various points along the pipe. The distance between the points A and B on the pipe was approximately eight feet, the propagation delay measured for that pipe section was approximately 8 nanoseconds, and pulses having a pulse width of 300 nanoseconds were employed.

FIG. 3 shows the leading edges 64, 66, 68, and 70 of the pulses corresponding to four locations on a length of known good pipe. In contrast, FIG. 4 depicts similarly measured and spaced leading edges 72, 74, 76, and 78 of four pulses corresponding to four locations on a section of the same pipe having visible surface corrosion.

In FIG. 3, the leading edges are fairly similar in shape, rise time, and amplitude and do not appear to be significantly shifted in time relative to each other, given that they were measured at different points along the pipe. In FIG. 4, the leading edges 72 and 74 appear to differ in shape, rise time, and amplitude from the leading edges 76 and 78, and at least the leading edge 74 appears to be significantly delayed in time relative to where it would be expected. Similar differences can be noticed by comparing the leading edges 72–78 with the leading edges 64–70.

The Applicant believes that these differences are caused by the surface corrosion on the pipe section with which the leading edges 72–78 are associated. The Applicant further believes that these leading edges 72–78 could have been used to predict corrosion if the condition of the pipe surface had not been known in advance.

EXAMPLE 2

Referring now to FIG. 5, depicted therein is a graph that plots against pipe length one factor relating to the leading edge of a series of modified pulses generated over a section of pipe 80 feet in length. The pipe tested was located in an operating oil refinery.

In particular, pipe distance in feet is plotted on the horizontal axis, while an amplitude in microvolts of the pulse adjacent to the pulse leading edges is plotted on the vertical axis. In this situation, the propagation delay was approximately 100 nanoseconds, while the pulse widths employed were approximately one microsecond. The pulses were timed to intersect at intersecting locations spaced approximately three inches apart.

For ease of comparison, the amplitude values plotted on the vertical axis have been normalized to a given voltage that is identified at zero.

The first 45 feet of pipe was above ground and easily accessible for visual inspection. This first 45 feet of pipe above ground was clearly in good condition. Between 45 and approximately 70 feet, the pipe was buried and its condition is unknown. Between approximately 70 feet and 80 feet, the pipe was partially above ground. At between approximately 70 and 72 feet, the pipe was visually corroded where it left the ground; the pipe appeared not to be corroded at between approximately 73 to 80 feet.

The buried pipe between approximately 45 and 70 feet crossed underneath a paved roadway and, as mentioned, it could not be examined to evaluate its condition. However, by comparing: (a) the amplitude values of the known good pipe (0–45 feet); (b) the amplitude values of the underground pipe (45–70 feet); and (c) the amplitude values of the known bad pipe (70–72 feet), the Applicant predicts that at least a portion of the buried pipe, between approximately 60 feet and 70 feet, is corroded and that a portion of the buried pipe, between approximately 45 feet and 60 feet, is not corroded.

Clearly, the amplitude readings for the section of the pipe between 60 feet and 72 feet are similar and quite different from those outside of the range; the inference can thus be made that the condition of the pipe between 60 and 70 feet is the same as that between 70 and 72 feet. One can similarly infer that, because the amplitude values from 0 to 60 feet and from 72 to 80 feet are generally similar, the condition of the pipe outside the range of 60 to 72 feet is also similar. Based on known pipe condition, the condition of unknown pipe can thus be predicted.

While knowledge of amplitude readings of known good and known bad pipe can be quite helpful in predicting anomalies, the applicant believes that such anomalies can be detected without knowledge of the condition of the pipe. This may be accomplished by, for example, looking for particular identifying pulse signatures that, from experience, appear to correspond to a given anomaly. This can also be accomplished by comparing one modified pulse with other similarly modified pulses to detect differences relating to waveform shape, rise time, amplitude, and/or time delay.

Thus, while in the examples set forth herein knowledge of the condition of at least a portion of the pipe is used to conclude that an anomaly does or does not exist in the rest of the pipe, the Applicant believes that this basic process is valid even if the condition of the entire pipe is unknown.

EXAMPLE 3

Referring now to FIGS. 6 and 7, a situation similar to that described in Example 2 set forth above is shown. Again, the pipe under test was in use in a refinery setting. In FIG. 6, distance along a given pipe is plotted against the horizontal axis, while a percentage change in amplitude values from a reference value is plotted against the vertical axis. In FIG. 7, distance for the same pipe is plotted against the horizontal axis, but zero feet in FIG. 7 corresponds to 80 feet in FIG. 8, and vice versa. Amplitude values referred to a reference value identified as zero are plotted against the vertical axis in FIG. 7.

In FIG. 6, a first plot is identified by reference character 80 and a reference plot is identified by reference character 82. A single plot 84 is shown in FIG. 7. A portion of the plot 80 corresponding to a known good section of pipe is identified by reference character 86 (25 to 80 feet), while in FIG. 7 the same known good section of pipe is identified by reference character 88 (0 to 55 feet). The plot portions corresponding to the remaining pipe are identified by reference character 90 in FIG. 6 and reference character 92 in FIG. 7. The pipe corresponding to these plot portions 90 and 92 is buried and its condition is not known.

These FIGS. 6 and 7 are of interest in that they tend to confirm the observations set forth above with respect to FIGS. 3, 4, and 5. In particular, the reference plot 82 in FIG. 6 is comprised of data calculated for known good cable (close to a perfect conductor). As would be expected, plot 82 shows that the change in amplitude along a good cable is very minimal. In contrast, the change in amplitude in the pipe, as shown by the plot 82, is relatively large, and the character of this amplitude change alters along the length of pipe. This supports the applicant's conclusion that something about the pipe condition affects the characteristics of the modified pulses.

The plots 80 and 84 are for the same length of pipe. The only difference between the two plots is that the starting location and ending location of the intersecting points are switched for the tests plotted in FIGS. 6 and 7. As one would expect, the regions 88 and 92 in FIG. 7 are switched relative to the similar regions 86 and 90 in FIG. 6. This indicates that the different amplitude values are consistently associated with the same locations on the pipe without regard to the specifics of the test set up to measure these values. The plots 80 and 84 also indicate that the system 20 used to ascertain anomalies along a give length of pipe yields repeatable results.

The graphs depicted in FIGS. 5–7 show just one rather simple method by which the raw data obtained from modified pulses can be processed to obtain information about the length of pipe under test. The process of extracting information from other characteristics of the modified pulses, such as rise time, waveform shape, and time displacement, can be quantified and plotted in a manner similar to those employed with amplitude in FIGS. 5–7.

SUMMARY

From the foregoing, it should be clear that other methods of processing the raw modified pulses can be used to highlight the information carried by these pulses. The basic principle is to look for any characteristics in the modified pulses that indicate localized changes in propagation velocity along the length of the pipe. While the information described herein related to the leading edges of these pulses contains such information, it may be possible to obtain this information from the shape of the entire pulse, the trailing edge, changes in pulse width, and other pulse characteristics that can be affected by changes in propagation velocity.

Accordingly, the present invention may be embodied in other specific forms without departing from the essential characteristics thereof. The present embodiments are therefore to be considered in all respects as illustrative and not restrictive, the scope of the invention being indicated by the appended claims rather than by the foregoing description; all changes which come within the meaning and range of equivalency of the claims are therefore intended to be embraced therein.

I claim:

1. A method of detecting an anomaly of a conductive member, comprising the steps of:
   sending first and second electrical pulses along the member from first and second locations towards an intersecting location such that the pulses intersect and are modified at the intersecting location;
   analyzing at least one indicator characteristic of a selected one of the modified pulses to ascertain whether an anomaly exists at the intersecting location, where the indicator characteristic is indicative of localized velocity changes of the selected pulse as it travels along the conductive member, wherein the step of analyzing the at least one characteristic of one of the modified pulses further comprises the steps of
   generating a coded representation of the selected pulse;
   processing the coded representation of the selected pulse to emphasize the indicator characteristic of the selected pulse.

2. A method as recited in claim 1, in which the step of analyzing at least one characteristic of at least one of the modified pulses comprises the steps of:
   selecting one of the modified pulses; and
   analyzing a waveform of the selected modified pulse.

3. A method as recited in claim 2, in which the step of analyzing at least one characteristic of at least one of the modified pulses comprises the steps of:
   selecting one of the modified pulses; and analyzing a shape of the waveform of the selected modified pulse.

4. A method as recited in claim 1, in which the step of analyzing at least one characteristic of at least one of the modified pulses comprises the steps of:
   selecting one of the modified pulses; and
   comparing the selected modified pulse with a reference modified pulse obtained at a different location on the elongate member.

5. A method as recited in claim 1, in which the step of analyzing at least one characteristic of at least one of the modified pulses comprises the steps of:
   selecting one of the modified pulses; and
   comparing the selected modified pulse with a reference modified pulse obtained at a reference location on the elongate member where no surface anomaly exists.

6. A method as recited in claim 1, further comprising the step of electrically connecting the first and second locations such that these locations are at substantially the same electrical potential.

7. A method as recited in claim 1, further comprising the steps of:
   providing test equipment to generate the steps of sending an electrical pulse and of analyzing at least one characteristic of at least one of the modified pulses; and
   referencing the test equipment to the electrical potential at one of the first and second locations.

8. A method as recited in claim 1, further comprising the step of:
   sending a pulse from the second location to the first location through the intersecting location to obtain a reference unmodified pulse at the first location;
   wherein the step of analyzing at least one characteristic of at least one of the modified pulses comprises the steps of:
   selecting the modified pulse that reaches first location; and
   comparing the selected modified pulse with the reference unmodified pulse.

9. A method as recited in claim 1, in which:
   the step of sending an electrical pulse along the member from first and second locations comprises the steps of
   sending a first pulse from the first location, and
   sending a second pulse from the first location, where the second pulse intersects with a third pulse sent from the second location; and
   the step of analyzing at least one characteristic of at least one of the modified pulses comprises the step of processing the modified third pulse based on the first pulse.

10. A method as recited in claim 9, further comprising the step of:
    sending a reference pulse from the second location to the first location through the intersecting location to obtain a reference unmodified pulse at the first location;
    wherein the step of analyzing at least one characteristic of at least one of the modified pulses comprises the step of comparing the processed modified second pulse with the reference unmodified pulse.

11. A method as recited in claim 1, in which:
    the step of sending an electrical pulse along the member from first and second locations comprises the steps of
    sending a first series of pulses from the first location,
    sending a second series of pulses from the second location, and
    timing the pulses in the first and second series such that a plurality of modified pulses are generated, one for a each of a plurality of intersecting locations; and
    the step of analyzing at least one characteristic of at least one of the modified pulses comprises the step of analyzing each of the modified pulses to ascertain the presence or absence of surface anomalies at the intersecting location associated with each of the modified pulses.

12. A method as recited in claim 11, in which the step of timing the pulses in the first and second series comprises the steps of:
    determining a propagation delay of electrical signals between the first and second locations on the elongate member; and
    generating the first and second series of pulses based on the propagation delay such that the pulses in the first and second series of pulses intersect at predetermined intersecting locations.

13. A method as recited in claim 1, in which the step of sending an electrical pulse along the member from first and second locations comprises the steps of:
    sending a first pulse from the first location;
    sending a second pulse from the second location; and
    coordinating the generation of the first and second pulses such that leading edges of the first and second pulses intersect at the intersecting location.

14. A method as recited in claim 1, further comprising the steps of:
    determining a propagation delay of electrical signals between the first and second locations on the elongate member;
    generating the electrical pulses applied to the first and second locations such that the duration of these electrical pulses is longer than the propagation delay.

15. A method as recited in claim 14, in which the step of generating the electrical pulses comprises the step of setting a duration of these electrical pulses that is at least ten times the propagation delay.

16. A method as recited in claim 1, in which the step of analyzing at least one characteristic of the electrical pulse comprises the step of analyzing at least one characteristics from a group of characteristics comprising absolute time location of a leading edge, rise time, and amplitude of a modified pulse.

17. A method of detecting corrosion of a length of insulated pipe, comprising the steps of:
   sending an electrical pulse along the length of insulated pipe from a first location to a second location;
   analyzing at least one indicator characteristic of the electrical pulse to ascertain whether corrosion exists along the length of insulated pipe, where the at least one characteristic is selected from a group of pulse characteristics indicative of localized velocity changes, wherein the step of analyzing the at least one characteristic of one of the modified pulses further comprises the steps of
      generating a coded representation of the electrical pulse;
      processing the coded representation of the electrical pulse to emphasize the indicator characteristic of the electrical pulse.

18. A method as recited in claim 1, in which the step of processing the coded representation of the selected pulse further comprises the step of comparing the coded representation of the selected pulse with a coded representation of a reference pulse.

19. A method as recited in claim 18, in which the reference pulse is an unmodified pulse that has passed through the elongate member.

20. A method as recited in claim 1, in which the step of processing the coded representation of the selected pulse further comprises the step of analyzing the amplitude of a given point on the selected pulse.

21. A method as recited in claim 1, in which the step of processing the coded representation of the selected pulse further comprises the step of plotting the amplitudes of a number of modified pulses against the length of the elongate member.

22. A method as recited in claim 1, in which the step of processing the coded representation of the selected pulse further comprises the step of comparing the amplitudes of modified pulses associated with other locations on the elongate member with the amplitude of the selected pulse.

23. A method as recited in claim 1, in which the step of plotting the amplitudes of a number of modified pulses against the length of the elongate member further comprises the step of plotting the amplitudes of the modified pulses at a given point on the pulses.

24. A method as recited in claim 21, in which the step of processing the coded representation of the selected pulse further comprises the step of comparing the amplitude of the selected pulse with the amplitudes of the other modified pulses.

25. A method as recited in claim 21, in which the step of processing the coded representation of the selected pulse further comprises the step of normalizing the amplitudes of the modified pulses.

26. A method as recited in claim 1, in which the step of processing the coded representation of the selected pulse further comprises the step of plotting a percentage change in amplitude values from a reference value.

27. A method as recited in claim 20, in which the given point on the electrical pulse is adjacent to the leading edge of the electrical pulse.

28. A method as recited in claim 17, in which the step of processing the coded representation of the electrical pulse further comprises the step of comparing the coded representation of the electrical pulse with a coded representation of a reference pulse.

29. A method as recited in claim 17, in which the step of processing the coded representation of the electrical pulse further comprises the step of analyzing the amplitude of a given point on the electrical pulse.

30. A method as recited in claim 29, in which the given point on the electrical pulse is adjacent to the leading edge of the electrical pulse.

* * * * *